United States Patent [19]

Beuhler et al.

[11] Patent Number: 4,636,314

[45] Date of Patent: * Jan. 13, 1987

[54] POLYMER BLENDED MEMBRANES

[75] Inventors: Allyson J. Beuhler, Indian Head Park; Anthony J. Polak, Lake Zurich, both of Ill.

[73] Assignee: UOP Inc., Des Plaines, Ill.

[*] Notice: The portion of the term of this patent subsequent to Feb. 19, 2002 has been disclaimed.

[21] Appl. No.: 590,294

[22] Filed: Mar. 16, 1984

[51] Int. Cl.$^4$ .............................................. B01D 13/00
[52] U.S. Cl. ................................ 210/500.25; 55/158
[58] Field of Search .................... 210/500.2, 505, 490, 210/491; 524/413; 204/129; 55/167, 158

[56] References Cited

U.S. PATENT DOCUMENTS

| | | | |
|---|---|---|---|
| 3,246,767 | 4/1966 | Pall et al. | 210/505 |
| 3,962,158 | 6/1976 | Mima et al. | 210/500.2 X |
| 4,024,036 | 5/1977 | Hakamura et al. | 204/129 |
| 4,500,667 | 2/1985 | Polak et al. | 524/413 X |

Primary Examiner—Frank Spear
Attorney, Agent, or Firm—Thomas K. McBride; John F. Spears, Jr.; Raymond H. Nelson

[57] ABSTRACT

Polymer blended membranes which comprise a blend of a compound such as a heteropoly acid or salt thereof and a polymer which is at least partially compatible with said compound, said blend containing a multiplicity of electrically conductive particles which form a portion of said membrane may be prepared by admixing the polymer and the acid or salt in a mutually miscible solvent. Thereafter, the electrically conductive particles, the size of which is sufficient so that the surfaces of the particles are coexistent with or extend beyond the surfaces of the membrane, may be added to the solution or, alternatively, the solution may be cast onto a casting surface and the particles added in a manner so as to ensure a uniform distribution of the particles throughout the solution. After evaporation of the solvent, the resulting thin film membrane may then be recovered and used in a gas separation apparatus or in a gas sensor apparatus.

29 Claims, No Drawings

# POLYMER BLENDED MEMBRANES

BACKGROUND OF THE INVENTION

Semipermeable membranes may be used for a wide variety of separations involving liquid-liquid separations, liquid-liquid solid separations and gas-gas separations. The membranes which are employed for these purposes usually comprise various organic polymers or mixtures of organic polymers either alone or supported on a porous backing material. For example, semipermeable membranes which are used in desalination processes can comprise cellulose acetate polymers composited on a porous support which acts as a backing for the membrane, thin film composite membranes comprising polymeric compounds such as polyethyleneimine, epiamine, polyethylene, polypropylene films also composited on a porous support such as a polysulfone member, etc. Likewise, gaseous separation membranes may comprise polymeric membranes of cellulose nitrate or cellulose acetate support membranes having a polymer such as dimethylsilicone, styrene, siliconcarbide compolymers composited thereon, as well as thin film membranes such as polymethylpentene polymers. In addition to these membranes other permselective membranes such as heteropoly acids may be employed for separating gases such as hydrogen from mixtures of gases in a gaseous stream.

In a majority of cases, the admixture of an organic compound, especially in a polymeric state, with an inorganic compound, results in a phase separation, the two systems being immiscible in nature. However, we have now discovered that a polymer blended membrane may be fabricated by admixing a heteropoly acid or a salt thereof with an organic polymer which is at least partially compatible with said heteropoly acid or salt thereof to form a polymer blended composition of matter which may be admixed with electrically conductive particles, the surfaces of said electrically conductive particles being coexistent with or extending beyond the surfaces of the resulting thin film membrane to form a composition which may be useful in gas separation processes. It was totally unexpected that a thin film membrane could be cast from the polymer blend to provide a membrane which could be highly selective to certain gases and therefore able to act as a proton conductor in a hydrogen separator in which molecular hydrogen is converted to proton on one side of the separation device, transported through the membrane and recombined as molecular hydrogen on the other side, while the electrically conductive particles would replace the external circuit of the device, thereby permitting electrons from one side of the separation device to travel through the particles to combine with hydrogen ions passing through the membrane on the surface of the particles.

BRIEF SUMMARY OF THE INVENTION

This invention relates to a composition of matter which may be used as gas separation membranes. More specifically, the invention is concerned with a novel thin film organic-inorganic membrane containing electrically conductive particles, said membrane being utilized in gas separation processes.

A conventional operation for separating certain gases from a gas stream containing a mixture of gases whereby a desired gas may be separated and recovered involves the use of membranes which possess a high permeability to the molecular form of the desired gas such as oxygen, hydrogen, nitrogen, etc. These membranes, especially in the case of hydrogen, possess a high permeability to hydrogen whereby molecular hydrogen is transported from the high pressure side of the device, through the membrane and emerges as molecular hydrogen on the low pressure side. Alternatively, separation of gases may be attained by dissociating the desired gas on the high pressure side and transporting it as an ion through the membrane followed by recombining the ions on the low pressure side. Therefore, a desirable membrane for hydrogen separation should possess excellent protonic conductivity properties. As will hereinafter be shown in greater detail, we have now discovered that membranes which contain both organic and inorganic components will possess this desired property and therefore may be used as hydrogen sensors, hydrogen separation devices, as well as solid state thin film electrolytes.

It is therefore an object of this invention to provide novel polymeric membranes which are useful in gas separation devices.

A further object of this invention is to provide a method for preparing organic-inorganic membranes of a type hereinafter set forth in greater detail, said membranes being utilized in gas separation devices.

In one aspect an embodiment of this invention resides in a thin film organic-inorganic membrane comprising a blend of a compound selected from the group consisting of heteropoly acids and salts thereof and a polymer which is at least partially compatible with said compound, said blend containing a multiplicity of electrically conductive particles forming a portion of said membrane, the particles being of a size sufficient so that the surfaces of said particles are coexistent with or extend beyond the surfaces of said membrane.

Another embodiment of this invention is found in a method for the preparation of a thin film organic-inorganic membrane which comprises dissolving a compound selected from the group consisting of heteropoly acids and salts thereof and a polymer which is at least partially compatible with said compound in a mutually miscible solvent at solution conditions for a period of time sufficient to form a blend, adding electrically conductive particles to said solution, admixing said solution and said particles, casting the blend containing said particles on a casting surface, removing said solvent and recovering the resultant membrane.

A specific embodiment of this invention includes a thin film organic-inorganic membrane comprising a blend of dodecamolybdophosphoric acid and poly(vinyl alcohol), said blend containing a multiplicity of electrically conductive particles comprising platinum deposited on a solid support comprising at least a monolayer of a carbonaceous pyropolymer comprising recurring units containing at least carbon and hydrogen atoms composited on the surface of a high surface area refractory inorganic metal oxide, said particles being of a size sufficient so that surfaces of said particles are coexistent or extend beyond said surfaces of said membrane.

Another specific embodiment of this invention is found in a method for the preparation of a thin film organic-inorganic membrane which comprises dissolving dodecamolybdophosphoric acid and poly(vinyl alcohol) in water at a temperature in the range of from about ambient to about 100° C. for a period of time sufficient to form a blend, adding thereto electrically conductive particles comprising platinum deposited on a solid support comprising at least a monolayer of a carbonaceous pyropolymer comprising recurring units containing at least carbon and hydrogen atoms composited on the surface of a high surface area refractory inorganic metal oxide, admixing said solution and said particles, casting the blend containing said particles on a casting surface, removing said water by evaporation, and recovering the resultant thin film membrane.

Other objects and embodiments will be found in the following further detailed description of the invention.

DETAILED DESCRIPTION OF THE INVENTION

As hereinbefore set forth, the present invention is concerned with a thin film organic-inorganic membrane comprising a polymeric blend of a heteropoly acid or salt thereof and an organic polymer which is at least partially compatible with said acid or salt, the blend of the two components containing, in addition thereto, a multiplicity of electrically conductive particles.

Heretofore, when attempting to blend an organic polymer with an inorganic compound, the usual result is to obtain a phase separation. In contradistinction to this, a single phase system may be obtained by admixing certain organic polymeric compounds with a heteropoly acid or salt thereof, the resulting composition of matter forming a thin film membrane which may be utilized in gas separation systems. The use of these membranes in gas separation devices is due in some respect to the fact that heteropoly acids or salts thereof possess a high protonic conductivity, especially at room or ambient temperature. The membranes which are formed from the blend of the organic polymer and the heteropoly acid or salt thereof possess excellent transport properties as well as an increase in tensile strength over those membranes prepared from pure organic polymers. The physical properties which these thin film membranes exhibit thus provide an attractive base for their use as gas sensors, especially in the case of hydrogen, or as gas separation membranes. As will hereinafter be shown in greater detail, the organic-inorganic blends possess chemical, mechanical and electrical properties which indicate the two materials form a single phase system. For example, the blends possess only one glass transition temperature which indicates a single phase system inasmuch as, if the resulting membranes were a two-phase system, or merely a physical mixture, the composition would possess two separate and distinct glass transition temperatures. In addition, the yield strength and modulus is greatly increased over those properties which are possessed by either of the two components. Another physical characteristic which indicates a single phase or true composition of matter is that the blend is transparent to visible light as well as being uniform in color.

The desired membrane of the present invention comprises a blend of an organic polymer which may be present in an amount in the range of from 99% to about 30% by weight of said blend and a heteropoly acid or salt thereof which may be present in an amount in the range of from about 1% to about 70% by weight of said blend, the polymer being at least partially compatible with the acid or salt, said blend containing a multiplicity of electrically conductive particles. Examples of organic polymers which may be employed as one component of the blend of the present invention include poly(vinyl alcohol), poly(vinyl fluoride), polyethylene oxide, polyethyleneimine, polyacrylic acid, polyethylene glycol, cellulose acetate, polyvinylmethylethyl ether, phenol formaldehyde resins, etc.

Examples of heteropoly acids or salts thereof which may be employed as the second component of the organic-inorganic blend which may be used to form a membrane will possess the generic formula:

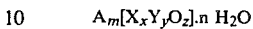

$$A_m[X_xY_yO_z].n\ H_2O$$

in which X and Y may be selected from the group consisting of boron, aluminum, gallium, silicon, germanium, tin, phosphorus, arsenic, antimony, bismuth, selenium, tellurium, iodine and the first, second, third and fourth transitional metal series, said series including scandium, yttrium, lanthanum, actinium, titanium, zirconium, hafnium, vanadium, niobium, tantalum, chromium, molybdenum and tungsten, X and Y being dissimilar in nature, Y being at least one metal selected from the first, second, third or fourth transition metal series above named, a is selected from the group consisting of hydrogen, ammonium, sodium, potassium, lithium, rubidium, cesium, beryllium, magnesium, calcium, strontium, and barium, m is an integer of from 1 to 10, y is an integer of from 6 to 12 based on x taken as 1, z is an integer of from 30 to 80 and n is an integer of from 3 to 100.

Specific examples of these compounds will include dodecamolybdophosphoric acid, ammonium molybdophosphate, sodium molybdophosphate, potassium molybdophosphate, lithium molybdophosphate, calcium molybdophosphate, magnesium molybdophosphate, dodecatungstophosphoric acid, ammonium tungstophosphate, sodium tungstophosphate, potassium tungstophosphate, lithium tungstophosphate, calcium tungstophosphate, magnesium tungstophosphate, dodecamolybdosilicic acid, ammonium molybdosilicate, sodium molybdosilicate, potassium molybdosilicate, lithium molybdosilicate, calcium molybdosilicate, magnesium molybdosilicate, dodecamolybdogermanic acid, ammonium molybdogermanate, sodium molybdogermanate, potassium molybdogermanate, lithium molybdogermanate, calcium molybdogermanate, magnesium molybdogermanate, hexamolybdotelluric acid, ammonium molybdotellurate, sodium molybdotellurate, potassium molybdotellurate, lithium molybdotellurate, calcium molybdotellurate, magnesium molybdotellurate, dodecatungstosilicic acid, ammonium tungstosilicate, sodium tungstosilicate, potassium tungstosilicate, lithium tungstosilicate, calcium tungstosilicate, magnesium tungstosilicate, etc. It is also contemplated within the scope of this invention that some uranyl compounds may also be employed as the heteropoly acid or salt thereof. These uranyl compounds will possess the generic formula:

$$A[UO_2]XO_4.n\ H_2O$$

in which A is selected from the group consisting of hydrogen, lithium, sodium potassium, ammonium, copper, magnesium, calcium, barium, strontium, lead, iron, cobalt, nickel, manganese, and aluminum, X is selected from the group consisting of phosphorus and arsenic and n is an integer of from 1 to 4. Some specific examples of these uranyl compounds will include uranyl orthophosphate, uranyl orthoarsenate, lithium uranylphosphate, lithium uranylarsenate, sodium uranylphosphate, sodium uranylarsenate, potassium uranylphosphate, potassium uranylarsenate, ammonium uranylphosphate, ammonium uranylarsenate, calcium uranylphosphate, calcium uranylarsenate, barium uranylphosphate, barium uranylarsenate, copper uranylphosphate, copper uranylarsenate, iron uranylphosphate, iron uranylarsenate, cobalt uranylphosphate, cobalt uranylarsenate, nickel uranylphosphate, nickel uranylarsenate, etc.

It is to be understood that the aforementioned listing of organic polymeric compounds, heteropoly acids or salts thereof are only representative of the class of compounds which may be employed in formulating the organic-inorganic blends of the present invention, and that this invention is not necessarily limited thereto.

The blend of the organic and inorganic materials of the type hereinbefore set forth will contain, in addition thereto, electrically conductive particles. The electrically conductive particles will possess the desirable characteristics of being able to catalyze the dissociation of certain gaseous elements, that is, the ability to transmit electrons through the particle from one surface thereof to a second surface thereof.

The electrically conductive particles which are admixed with the blend will possess the ability to catalyze the dissociation of certain gaseous elements, mainly hydrogen, although it is also contemplated that gaseous hydrocarbons such as methane, ethane, propane, etc. may also undergo dissociation when subjected to the action of these particles. In the preferred embodiment of the invention the electrically conductive particles will comprise metals of Group VIII of the Periodic Table or alloys of these metals, either with themselves or with other metals. Especially preferred are the metals such as platinum, palladium, ruthenium or nickel or alloys such as platinum-nickel, palladium-nickel, copper-nickel, ruthenium-nickel, etc. The electrically conductive particles may consist of these metals per se in their elemental state or the metals may be deposited on a solid support which itself may possess some electrically conductive properties. An example of this type of electrically conductive support comprises a solid composite comprising at least a monolayer of a carbonaceous pyropolymeric structure comprising recurring units containing at least carbon and hydrogen atoms on the surface of a substrate which itself comprises a high surface area refractory inorganic oxide. This high surface area refractory inorganic oxide will possess a surface area in the range of from about 1 to about 500 m$^2$/g and will include refractory oxides such as alumina in various forms including gamma-alumina, beta-alumina, theta-alumina or mixtures of inorganic refractory oxides such as silica-alumina, silica-zirconia, zirconia-titania, zirconia-alumina, zeolites, etc. The shape of the inorganic support upon which the carbonaceous pyropolymer is deposited can be in any form desired and may be obtained by any method known in the art such as marumerizing, pelletizing, nodulizing, etc.

In one method of preparing the composite, the inorganic support is heated to a temperature of from about 400° to about 1200° C. in a reducing atmosphere containing an organic pyrolyzable compound. The organic pyropolymer precursors most commonly and preferably used are compounds of the group consisting of aliphatic hydrocarbons such as alkanes including ethane, propane, butane, etc; alkenes including ethylene, propylene, the isomeric butylenes; alkynes such as ethyne, propyne, 1-butyne, etc; aliphatic halogen derivatives such as chloromethane, bromomethane, carbon tetrachloride, chloroform, etc.; aliphatic oxygen derivatives such as methanol, ethanol, propanol, glycol, ethyl ether, formic acid, acetic acid, acetone, formaldehyde, etc.; aliphatic sulfur derivatives such as methyl mercaptan, ethyl mercaptan, n-propyl mercaptan, etc.; aliphatic nitrogen derivatives such as nitroethane, nitropropane, acetomide, dimethylamine, etc.; alicyclic compounds such as cyclohexane, cycloheptane, cyclohexene, etc.; aromatic compounds such as benzene, toluene, benzyl chloride, anisole, benzaldehyde, acetophenone, phenone, benzoic acid, etc.; and heterocyclic compounds such as furan, pyran, coumarin, etc. As can be seen, an extremely wide latitude can be exercised in the selection of the organic pyrolyzable substances, since virtually any organic material that can be vaporized, decomposed and polymerized on the refractory oxide upon heating will suffice. The resultant carbonaceous pyropolymer will possess recurring units containing at least carbon and hydrogen atoms; however, depending upon the pyropolymer precursor which has been selected, the pyropolymer may also contain other atoms such as nitrogen, oxygen, sulfur or metals such as an organometallic compound have been used as the pyropolymer precursor.

In another embodiment, the composite may be prepared by impregnating the refractory inorganic oxide substrate with a solution of a carbohydrate material such as dextrose, sucrose, fructose, starch, etc., and thereafter drying the impregnated support. After drying, the impregnated support is then subjected to pyrolysis temperatures within the range hereinbefore set forth whereby a carbonaceous pyropolymer similar in nature to those hereinbefore described is formed in at least a monolayer on the surface of the refractory inorganic oxide support.

The support thus formed may then be impregnated with solutions or cosolutions of the metals of Group VIII of the Periodic Table to provide the desired electrically conductive particles. After obtaining the desired particle size, the thickness of which will hereinafter be set forth in greater detail by any means known in the art such as grinding, pulverizing, etc. whereby the support is formed in the desired particle size, the impregnation may be effected by treating the support with an aqueous or organic solution of the desired metal to deposit said metal on the surface of the carbonaceous pyropolymer support. The solution which is utilized to impregnate the carbonaceous pyropolymer support is preferably aqueous in nature, some specific examples of these aqueous solutions being chloroplatinic acid, chloroplatinous acid, bromoplatinic acid, platinic chloride, platinous chloride, as well as corresponding solutions of palladium, ruthenium, nickel, etc. After impregnation of the structure, the solvent may be removed by heating to a temperature in the range of from about 100° to about 400° C. depending upon the nature of the particular solvent in which the metal compound is dissolved, said temperature being that which is sufficient to evaporate the solvent and leave the metal impregnated on the surface of the carbonaceous pyropolymer structure. Thereafter, the structure may then be dried at elevated temperatures ranging from about 100° to about 200° C. for a period of time ranging from about two to about six hours or more. Following this, the metal impregnated carbonaceous pyropolymer support may then be subjected to a reducing step in the presence of a reducing atmosphere or medium such as hydrogen at elevated temperatures of from about 200° to about 600° C. or more for a period of time ranging from about 0.5 to four hours or more whereby the metallic compound is reduced to the elemental metal stage.

The size of the electrically conductive particles which are to be admixed with the polymeric blend hereinbefore described will be of a sufficient magnitude so that when forming the thin film membrane, which said particles form an integral portion, the surfaces of said particles will be coexistent with or extend beyond the surfaces of the thin film polymer blend which forms another integral portion of the membrane. As hereinbefore set forth, the thickness of the thin film membrane will range from about 0.1 to about 50 microns and preferably from about 5 to about 20 microns. Therefore, the thickness of the metal or metal-coated particles should range from about 0.5 to about 55 microns.

The novel thin film organic-inorganic membrane of the present invention may be prepared by admixing the two components of the blend, that is, the heteropoly acid or salt thereof and the polymer compound which is at least partially compatible with said acid or salt, in a mutually miscible solvent at solution conditions for a period of time sufficient to form the desired blend. In the preferred embodiment of the invention, the mutually miscible solvent which is employed to dissolve the components therein comprises water, although it is also contemplated within the scope of this invention that any other mutually miscible solvent either organic or inorganic in nature may also be employed. The admixing of the two components of the blend may be effected at solution conditions which will include a temperature in the range of from about ambient (20°-25° C.) up to the boiling point of the mutually miscible solvent which, for example, in the case of water is 100° C. The electrically conductive particles are added to the solution and the solution is subjected to a thorough admixing by any means such as stirring, shaking, rotating, etc. In addition, in the preferred embodiment of the invention, a dispersing agent of any type well known in the art may also be added to the solution to ensure that the particles do not tend to clump together or agglomerate, but will be uniformly dispersed throughout the solution. The time of reaction which is necessary to form the desired blend will vary with the particular organic polymers and heteropoly acids or salts thereof as well as the solvent and may be within a period of time ranging from about 0.5 up to about 10 hours or more in duration. Upon completion of the reaction period, the blend may then be cast upon a suitable casting surface which may consist of any suitable material possessing the desired properties so as to provide a surface free of any defects which may cause any imperfections on the surfaces of the membrane. Examples of suitable casting surfaces which may be employed may include metals such as stainless steel, aluminum, etc. glass, ceramics or polymers. After casting the solution upon the surface, the solvent may then be removed by any conventional means including natural evaporation or forced evaporation by the application of elevated temperatures to the casting surface whereby said solvent is evaporated and the desired membrane, comprising a thin film of the polymeric blend containing the electrically conductive particles uniformly dispersed therethrough, is formed. Alternatively, the membrane may also be formed by reprecipitation of the solution in a nonsolvent. Examples of nonsolvents which may be employed in the reprecipitation of the blend will include lower alcohols such as methanol, ethanol, propanol, etc.; paraffinic hydrocarbons such as pentane, hexane, heptane, etc.; chlorinated hydrocarbons such as chloroform, bromoform, carbon tetrachloride, dichlorobenzene, methylene chloride, etc.; ketones such as acetone, methyl ethyl ketone, methyl propyl ketone, etc.; carboxylic acids such as formic acid, acetic acid, propionic acid, trichloroacetic acid, etc.; esters such as methyl acetate, ethyl acetate, methyl acrylate, methyl methacrylate, etc.; tetrahydrofuran, etc.; as well as concentrated aqueous salt solutions. It is to be understood that the particular nonsolvent which is employed will be dependent upon the particular polymer and heteropoly acid or salt thereof which is being blended to form the desired inorganic-organic polymer blend.

In the preferred embodiment of the invention, the polymeric blend of the organic-inorganic compound will possess a molecular weight ranging from about 2000 up to about 135,000 or more and preferably greater than about 10,000. The thickness of the film can be controlled by the amount of heteropoly acid or salt thereof and/or the polymer which is present in the reaction mixture as well as the size of the particles of the electrically conductive material. In this respect, it is to be noted that the ratio of heteropoly acid or salt thereof and the organic polymer may vary over a relatively wide range. For example, the heteropoly acid or salt thereof may be present in the blend in a range of from about 1% to about 70% by weight of the blend while the organic polymer may be present in an amount in the range of from about 99% to about 30% by weight of the blend, the preferred ranges being from about 10% to about 70% for the heteropoly acid or salt and about 90% to about 30% for the organic polymer. The thin film organic-inorganic blend which may be prepared according to the process of the present invention may possess a thickness which may range from about 0.1 to about 50 microns in depth, and preferably from about 5 to about 20 microns.

As an alternate method of preparing the membrane of the present invention, the heteropoly acid or salt thereof and the organic polymer may be admixed in a manner similar to that hereinbefore set forth at solution conditions and allowed to react for a period of time necessary to form the desired blend. The blend may then be cast upon a suitable casting surface and the electrically conductive particles may then be added to the blend upon the casting surface in such a manner so as to ensure an even and uniform distribution of the particles throughout the blend. Following this, the solvent is then allowed to evaporate and the resulting membrane recovered. The solvent may also be removed by reprecipitation of the solution in a nonsolvent of the type hereinbefore set forth.

As a specific example of a method for preparing the membranes of the present invention, a predetermined amount of each of the components of the blend, namely the organic polymer and the heteropoly acid or salt thereof, is placed in an appropriate apparatus such as a flask. After heating of the mutually miscible solvent and dissolution of the components of the blend has been accomplished, the particles of the electrically conductive material of the type hereinbefore set forth may be added, and after thorough admixing thereof, the mixture is allowed to remain for the period of time necessary to accomplish a blend and thereafter cast upon an appropriate casting surface. As a more specific example, poly(vinyl alcohol) and dodecamolybdophosphoric acid may be placed in a flask and dissolved in water which has been heated to a temperature of 100° C. Thereafter particles of an electrically conductive material such as platinum composited on the surface of a solid support comprising at least a monolayer of a carbonaceous pyropolymeric structure comprising recurring units containing at least carbon and hydrogen atoms on the surface of a substrate which itself comprises a high surface area refractory inorganic oxide may be added and the solution thoroughly admixed by shaking. Upon completion of the desired residence time, the solution is cast upon an appropriate casting surface such as glass and the water is removed. The resulting polymer blend membrane containing the electrically conductive particles which form a portion of the membrane and whose surfaces are coexistent or extend beyond the surfaces of the polymer blend is then recovered and utilized in an appropriate gas separation apparatus or gas sensor apparatus.

Examples of novel thin film organic-inorganic polymer blends containing electrically conductive material such as particles of platinum, palladium, nickel or alloys thereof in their elemental state or deposited on a solid support which may be prepared according to the process of this invention will include poly(vinyl alcohol)-dodecamolybdophosphoric acid, poly(vinyl fluoride)-dodecamolybdophosphoric acid, cellulose acetate-dodecamolybdophosphoric acid, polyethylene oxide-dodecamolybdophosphoric acid, polyethylene glycol-dodecamolybdophosphoric acid, poly(vinyl alcohol)-dodecatungstophosphoric acid, poly(vinyl fluoride)-dodecatungstophosphoric acid, cellulose acetate-dodecatungstophosphoric acid, pdlyethylene oxide-dodecatungstophosphoric acid, polyethylene glycol-dodecatungstophosphoric acid, poly(vinyl alcohol)-dodecamolybdosilicic acid, poly(vinyl fluoride)-dodecamolybdosilicic acid, cellulose acetate-dodecamolybdosilicic acid, polyethylene oxide-dodecamolybdosilicic acid, polyethylene glycol-dodecamolybdosilicic acid, poly(vinyl alcohol)-ammonium molybodphosphate, poly(vinyl fluoride)-ammonium molybdophosphate, cellulose acetate-ammonium molybdophosphate, polyethylene oxide-ammonium molybdophosphate, polyethylene glycol-ammonium molybdophosphate, poly(vinyl alcohol)-uranyl orthophosphate, poly(vinyl fluoride)-uranyl orthophosphate, cellulose acetate-uranyl orthophosphate, polyethylene oxide-uranyl orthophosphate, polyethylene glycol-uranyl orthophosphate, etc. It is to be understood that the aforementioned list of polymer blends is only representative of the class of polymer blend membranes which may be prepared according to the process of this invention and that said invention is not necessarily limited thereto.

The membranes comprising a blend of a heteropoly acid or salt thereof and an organic polymer which contains the electrically conductive particles, the surfaces of which are coexistent with or extend beyond the surfaces of the blend may be utilized as a flat surface or in a tubular form. The tubing which comprises the polymer blend containing the electrically conductive particles may be fabricated by forcing a solution through a die while making provision for maintaining a hollow core. When this type of construction is desired, the electrically conducting particles may be added to the solution before the tube is formed, one surface of each particle being exposed to the interior of the tubing while a second surface of the particle which is in common with the external surface of the tubing is coexistent therewith or extends beyond. The size of the tube which is formed may vary over a relatively wide range, the wall thickness of the tubing varying depending upon the application.

The following examples are given for purposes of illustrating the novel membranes of the present invention as well as to a method for the manufacture thereof. However, it is to be understood that these examples are merely illustrative in nature and that the present process is not necessarily limited thereto.

EXAMPLE I

A novel polymer blended membrane was prepared by placing 0.25 gram of poly(vinyl alcohol) and 0.25 gram of dodecamolybdophosphoric acid in a flask. Twenty ml of deionized water was placed in the flask which was then heated to a temperature sufficient to dissolve both the polymer and the acid. After a time sufficient to form a blend, the solution was poured into a Petrie dish and cobalt particles were added, the amount of particles added being sufficient to impart a uniform distribution of particles throughout the film. The water was allowed to evaporate for a period of 16 hours and the resulting membrane which had a thickness of 20 microns was removed. To form a membrane in which the electrically conductive particles possess the ability to form protons, platinum was sputtered on the membrane surface using a conventional sputtering technique, both sides of the membrane being subjected to said sputtering.

EXAMPLE II

In this example, a membrane was prepared using the technique hereinbefore described in Example I above, that is, 0.25 gram of poly(vinyl alcohol) and 0.25 gram of dodecamolybdophosphoric acid being placed in a flask and adding thereto 20 ml of deionized water. The flask was then heated to a temperature sufficient to permit the dissolution of the polymer and the acid and the resulting solution was then poured onto a casting surface comprising a Petrie dish. Following this, electrically conductive particles comprising platinum deposited on a solid support consisting of at least a monolayer of a carbonaceous pyropolymeric structure comprising recurring units containing at least carbon and hydrogen atoms on the surface of a high surface area alumina substrate were added to the solution in a manner so as to ensure a uniform and even distribution of the particles throughout the polymer blend. After the water had evaporated, the resulting membrane was peeled off the dish and recovered.

EXAMPLE III

In a manner similar to that hereinbefore described, equimolecular amounts of uranyl orthophosphate and poly(vinyl alcohol) may be placed in a flask, deionized water may then be added thereto and the flask heated until both the heteropoly acid salt and the polymer are dissolved. Following this, nickel particles may be added to the solution which is thereafter thoroughly admixed to ensure an even distribution of the nickel particles throughout said solution. The resulting mixture may then be cast onto a casting surface and the solvent which comprised water, may be allowed to evaporate. After evaporation of the water, the resulting thin film membrane may then be recovered.

EXAMPLE IV

A thin film membrane may be prepared by admixing equal molecular weights of dodecamolybdophosphoric acid and cellulose acetate in a solvent comprising deionized water, the temperature of the water being sufficient to permit the acid and polymer to dissolve therein. The resulting solution may then be cast on a casting surface of a type hereinbefore described and particles of an electrically conducting material comprising elemental ruthenium may then be dispersed in a uniform manner throughout the solution. The water may be allowed to evaporate for a period of 16 hours following which the resulting film may be recovered.

We claim as our invention:

1. A thin film membrane comprising a single phase blend of: (1) from 1% to 70% by weight of a heteropoly acid or salts thereof having the generic formula:

$$A_m[X_xY_yO_z] \cdot nH_2O,$$

in which X is selected from the group consisting of boron, aluminum, gallium, silicon, germanium, tin, phosphorus, arsenic, antimony, bismuth, selenium, tellurium, iodine, and metals of the first, second, third, and fourth transitional metal series of the Periodic Table, where Y is dissimilar from X and is selected from at least one metal of the first, second, third, and fourth transitional metal series of the Periodic Table, where A is selected from the group consisting of hydrogen, ammonium, sodium, potassium, lithium, rubidium, cesium, beryllium, magnesium, calcium, strontium and barium, where m is an integer of from about 1 to 10, where y is an integer of from 6 to 12 based on x being equal to 1, where z is an integer of from 30 to 80, and where n is an integer of from 3 to 100 and, (2) from 99% to 30% by weight of a polymer compatible with said compound selected from the group consisting of poly(vinyl alcohol), poly(vinyl fluoride), polyethylene oxide, polyethyleneimine, polyacryclic acid, polyethylene glycol, cellulose acetate, polyvinylmethylethyl ether and phenol formaldehyde resins, said blend containing a multiplicity of electrically conductive particles forming a portion of said membrane, the particles being of a size sufficient so that portions of the surfaces of each of said particles are coexistent with or extend beyond each opposing surface of said membrane.

2. The membrane as set forth in claim 1 in which said membrane possesses a thickness in the range of from about 0.1 to about 50 microns.

3. The membrane as set forth in claim 1 in which said heteropoly acid comprises dodecamolybdophosphoric acid and said polymer comprises poly(vinyl alcohol).

4. The membrane as set forth in claim 1 in which said heteropoly acid comprises dodecamolybdophosphoric acid and said polymer comprises cellulose acetate.

5. The membrane as set forth in claim 1 in which said salt of a heteropoly acid comprises uranyl orthophosphate and said polymer comprises poly(vinyl alcohol).

6. The membrane as set forth in claim 1 in which said electrically conductive particles possess the ability to form a proton.

7. The membrane as set forth in claim 6 in which said electrically conductive particles comprise a metal or alloys thereof of Group VIII of the Periodic Table.

8. The membrane as set forth in claim 7 in which said metal or alloy thereof of Group VIII of the Periodic Table is deposited on a solid support.

9. The membrane as set forth in claim 8 in which said solid support comprises at least a monolayer of a carbonaceous pyropolymer comprising recurring units containing at least carbon and hydrogen atoms composited on the surface of a high surface area refractory inorganic metal oxide.

10. The membrane as set forth in claim 7 in which said metal of Group VIII of the Periodic Table comprises platinum.

11. The membrane as set forth in claim 7 in which said metal of Group VIII of the Periodic Table comprises palladium.

12. The membrane as set forth in claim 7 in which said metal of Group VIII of the Periodic Table comprises an alloy of platinum and nickel.

13. The membrane as set forth in claim 1 wherein the thickness of the membrane ranges from about 0.1 to about 50 microns.

14. The membrane as set forth in claim 1 wherein the thickness of said electrically conductive particles range from about 0.5 to about 55 microns.

15. A method for the preparation of a thin film organic-inorganic membrane which comprises dissolving in a mutually miscible solvent at solution conditions for a period of time sufficient to form a single phase blend (1) a heteropoly acid or salt thereof having the generic formula:

$$A_m[X_xY_yO_z] \cdot nH_2O,$$

in which X is selected from the group consisting of boron, aluminum, gallium, silicon, germanium, tin, phosphorus, arsenic, antimony, bismuth, selenium, tellurium, iodine, and metals of the first, second, third, and fourth transitional metal series of the Periodic Table, where Y is dissimilar from X and is selected from at least one metal of the first, second, third, and fourth transitional metal series of the Periodic Table, where A is selected from the group consisting of hydrogen, ammonium, sodium, potassium, lithium, rubidium, cesium, beryllium, magnesium, calcium, strontium and barium, where m is an integer of from about 1 to 10, where y is an integer of from 6 to 12 based on x being equal to 1, where z is an integer of from 30 to 80, and where n is an integer of from 3 to 100 and, (2) a polymer selected from the group consisting of poly(vinyl alcohol), poly(vinyl fluoride), polyethylene oxide, polyethyleneimine, polyacryclic acid, polyethylene glycol, cellulose acetate, polyvinylmethylethyl ether and phenol formaldehyde resins, casting said blend on a casting surface, removing said solvent and recovering the resultant membrane, said heteropoly acid or salt being employed in said blend in an amount of from 1% to 70% by weight and said polymer being employed in an amount of from 99% to 30% by weight, each based on the total weight of the heteropoly acid or salt and the polymer, said blend including electrically conductive particles being of a size sufficient and said membrane being cast of a thickness so that portions of the surfaces of each of said particles are coexistent with or extend beyond each opposing surface of said membrane.

16. The method as set forth in claim 15 in which said solution conditions include a temperature in the range of from about ambient to about 100° C.

17. The method as set forth in claim 15 in which said solution contains a dispersing agent.

18. The method as set forth in claim 15 in which said mutually miscible solvent comprises water.

19. The method as set forth in claim 18 in which the removal of said water is by evaporation.

20. The method as set forth in claim 15 in which the removal of said solvent is accomplished by reprecipitation in a nonsolvent.

21. The method as set forth in claim 15 in which said particles comprise a metal of Group VIII of the Periodic Table.

22. The method as set forth in claim 21 in which said metal of Group VIII of the Periodic Table is deposited on a solid support.

23. The method as set forth in claim 22 in which said solid support comprises at least a monolayer of a carbonaceous pyropolymer comprising recurring units containing at least carbon and hydrogen atoms composited on the surface of a high surface area refractory inorganic metal oxide.

24. The method as set forth in claim 21 in which said metal of Group VIII of the Periodic Table comprises platinum.

25. The method as set forth in claim 21 in which said metal of Group VIII of the Periodic Table comprises palladium.

26. The method as set forth in claim 15 in which said heteropoly acid comprises dodecamolybdophosphoric acid and said polymer comprises poly(vinyl alcohol).

27. The method as set forth in claim 15 in which said salt of a heteropoly acid comprises uranyl orthophosphate and said polymer comprises poly(vinyl alcohol).

28. The method as set forth in claim 15 wherein the thickness of said membrane ranges from about 0.1 to about 50 microns.

29. The method as set forth in claim 15 wherein the thickness of said electrically conductive particles ranges from about 0.5 to about 55 microns.

* * * * *